(12) United States Patent
Chen et al.

(10) Patent No.: US 11,572,577 B2
(45) Date of Patent: Feb. 7, 2023

(54) **FERMENTATION METHOD FOR PRODUCTION OF FUCOXANTHIN BY *NITZSCHIA LAEVIS***

(71) Applicant: Peking University, Beijing (CN)

(72) Inventors: Feng Chen, Beijing (CN); Bin Liu, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 320 days.

(21) Appl. No.: 16/310,367

(22) PCT Filed: Jun. 29, 2018

(86) PCT No.: PCT/CN2018/093490
§ 371 (c)(1),
(2) Date: Dec. 14, 2018

(87) PCT Pub. No.: WO2019/001548
PCT Pub. Date: Jan. 3, 2019

(65) Prior Publication Data
US 2021/0222216 A1    Jul. 22, 2021

(30) Foreign Application Priority Data

Jun. 30, 2017  (CN) .......................... 201710523735.6
Jun. 30, 2017  (CN) .......................... 201710525234.1
Jun. 15, 2018  (CN) .......................... 201810621986.2
Jun. 15, 2018  (CN) .......................... 201810623831.2

(51) Int. Cl.
*C12P 17/02*     (2006.01)
*C12N 1/12*      (2006.01)

(52) U.S. Cl.
CPC ............... *C12P 17/02* (2013.01); *C12N 1/12* (2013.01); *C12N 2500/05* (2013.01); *C12N 2500/34* (2013.01); *C12N 2500/38* (2013.01); *C12N 2500/60* (2013.01); *C12N 2500/74* (2013.01)

(58) Field of Classification Search
None
See application file for complete search history.

(56) References Cited

U.S. PATENT DOCUMENTS

2013/0309719 A1* 11/2013 Griffiths ................... C12N 1/12
435/257.1

FOREIGN PATENT DOCUMENTS

CN    103396979 B  * 11/2014

OTHER PUBLICATIONS

Guo, Bingbing, et al. "Screening of diatom strains and characterization of Cyclotella cryptica as a potential fucoxanthin producer." Marine Drugs 14.7 (2016): 125. (Year: 2016).*

* cited by examiner

*Primary Examiner* — Robert J Yamasaki
(74) *Attorney, Agent, or Firm* — Cantor Colburn LLP

(57) ABSTRACT

The invention discloses a fermentation method for production of fucoxanthin by *Nitzschia laevis*, including the following steps of: step A, preparation of inocula; step B, fermentation culture: inoculating of *Nitzschia laevis* according to a certain volume ratio to reaction kettle containing sterile fermentation medium for aeration fermentation, preparing fucoxanthin fermentation broth through culture mean of fed-batch nutrient components; step C, obtaining high fucoxanthin induction culture solution by aeration induction culture under irradiation of monochromatic light or mixed light; extracting fucoxanthin from high fucoxanthin induction culture solution. The invention optimized fermentation condition by fed-batch nutrient components during aeration culture of alga *Nitzschia laevis*, thereby significantly increasing the cell density of *Nitzschia laevis* in sterile fermentation broth, and then treating high density fucoxanthin induction culture solution of *Nitzschia laevis* by using light treatment, inducing the accumulation of fucoxanthin, thereby further increasing productivity of fucoxanthin produced by fermentation.

14 Claims, 3 Drawing Sheets

FERMENTATION METHOD FOR PRODUCTION OF FUCOXANTHIN BY NITZSCHIA LAEVIS

TECHNICAL FIELD

The present invention relates to the field of microbial fermentation. More specifically, the present invention relates to a fermentation method for production of fucoxanthin by *Nitzschia laevis*.

This application claims priority to Chinese Patent Application Number 201710523735.6, filed on Jun. 30, 2017, Chinese Patent Application Number 201710525234.1, filed on Jun. 30, 2017, Chinese Patent Application Number 201810621986.2, filed on Jun. 15, 2018, and Chinese Patent Application Number 201810623831.2, filed on Jun. 15, 2018.

BACKGROUND

Fucoxanthin is mainly derived from large seaweed and microalgae such as *Laminaria japonic*, diatoms and golden algae. It is a natural carotenoid and participates in reaction of photosynthesis. Fucoxanthin harbors a very unique structure with an allenic bond endowing fucoxanthin with special properties. In recent years, studies have found that fucoxanthin has multiple functional activities in cells, animals, and humans, including antioxidant, anti-inflammatory, anti-cancer, anti-obesity, anti-diabetic, anti-angiogenic, and anti-malarial activities. It has protective effects on organs such as liver, brain blood vessels, bones, skin and eyes. Based on the above functions, fucoxanthin is a natural product with broad prospects for health food and drug development. The market capacity of fucoxanthin is 500 tons, and the price of a 10% fucoxanthin extract (w/w) reaches over 40,000 RMB/kg. Therefore, it has great market value.

The significant role of fucoxanthin in weight loss has attracted more and more attention. It can achieve weight loss by inhibiting the formation of fat cells and accelerating fat catabolism. Currently, fucoxanthin is mainly extracted from large seaweeds such as *Undaria pinnatifida* and *Laminaria japonica*. However, the use of marine macroalgae as a source of fucoxanthin has important shortcomings, such as thick cell wall, high polysaccharide content, difficulty in purification, and marine pollution. Furthermore, the fucoxanthin content in seaweeds is extremely low (only 0.01%-0.07% of cell dry weight), which limits its application. The content of fucoxanthin in marine microalgae reach up to 0.6% (of cell dry weight), which is nearly 100 times that of large seaweeds. Therefore, microalgae are better alternative sources of fucoxanthin.

*Nitzschia laevis* is a unicellular alga belonging to Bacillariophyta. There are few studies on the production of fucoxanthin by *Nitzschia laevis*. The applicant's previous research found that the *Nitzschia laevis* had the highest fucoxanthin productivity of 9.88 mg/(L·d), and could be cultured heterotrophically without light (Application Number: 201710523735.6). *Nitzschia laevis*, a unicellular plant, contained a fucoxanthin content of up to 1.38% (of dry cell weight) with autophototrophic culture, but the biomass concentration is very low, usually less than 1 g/L (Patent Application Number: 201710525234.1). After fermentation optimization, the cell density of *Nitzschia laevis* was up to 21.2 g/L, which was 20-30 times that of autophototrophic culture. However, the fucoxanthin content in the cells after fermentation was only 0.75% (accounting for dry weight of cell). It is only half of the culture under autophototrophic culture conditions. Therefore, how to effectively improve the fucoxanthin content in the *Nitzschia laevis* fermentation broth prepared by heterotrophic culture has become one of the technical problems to be solved in this process.

The applicant found through retrieving that Qi (2015) found different light quality (blue light, green light and red light) had significant effects on fucoxanthin content of the diatom *Phaeodactylum tricornutum* under autophototrophic culture conditions (Chinese Marine Science, 2015, 39(7): 1-6). Red light promoted the growth of *Phaeodactylum tricornutum* and increased the content of fucoxanthin, while green light and blue light inhibited cell growth and reduced the content of fucoxanthin. However, *Phaeodactylum tricornutum* was cultured by continuous irradiation of monochromatic light. Heui-Chun et al. studied the effects of different light qualities (blue, green, red and white) on the accumulation of fucoxanthin in the *Chaetoceros calcitrans*, and found that blue light stimulated the accumulation of fucoxanthin. Red light inhibited the accumulation of fucoxanthin. But this research used *Chaetoceros calcitrans*, and used continuous irradiation culture through monochromatic light. There was rare investigation on the heterotrophic culture characteristics of algae and the effects of cells after fermentation on the accumulation of fucoxanthin. (Bulletin of the Korean Society of Fisheries Technology, 2014, 50: 447-454). To the best of applicants' knowledge, this is the first effort to figure out the effect of light quality on fucoxanthin accumulation of in *Nitzschia laevis*.

DESCRIPTION

A purpose of the present invention is to solve at least the above problems and provide at least the advantages which will be described later.

Another purpose of the present invention is to provide a fermentation method for production of fucoxanthin by *Nitzschia laevis*. The preparation method optimized fermentation conditions by fed-batch nutrient components during aeration culture of *Nitzschia laevis* to significantly improve the cell density in sterile fermentation broth. And then, light was supplied to induce fucoxanthin accumulation and further improve the productivity of fucoxanthin.

In view of purposes mentioned above and other advantages, the present invention provides a fermentation method for production of fucoxanthin by *Nitzschia laevis*, including the following steps of:

step A, preparation of the inocula:

placing activated alga *Nitzschia laevis* in a sterile inocula culture medium, performing heterotrophic culture for 2-11 days to prepare the inocula, making *Nitzschia laevis* cells in logarithmic growth phase, wherein the alga *Nitzschia laevis* is selected from *Nitzschia laevis* CCMP559, *Nitzschia laevis* UTEX 2047, or *Nitzschia laevis* CCMP 1092, wherein *Nitzschia laevis* is selected from *Nitzschia laevis* UTEX 2047 (purchased from Culture Collection of Algae at the University of Texas at Austin, abbreviating UTEX);

step B, fermentation culture:

inoculating of *Nitzschia laevis* in the logarithmic growth phase of the step A according to a volume ratio of 3%-20% to a reaction kettle containing a sterile fermentation medium for aeration fermentation, preparing fucoxanthin fermentation broth through culture mean of fed-batch nutrient components, wherein the temperature is 20 to 30 degree Celsius in the aeration fermentation process, fermentation cycle is 2-14 days, dissolved oxygen of the fermentation medium is not less than 20%, pH is 6-9, and the concentration of glucose, nitrate and phosphate in the fermentation medium is 1-10 g/L, 0.1-1.5 g/L and 10-100 mg/L, respectively; wherein the reaction kettle of aeration fermentation is a stirred fermenter, and stirring speed of the stirred fermenter is 100-750 rpm during the aeration fermentation process, introducing sterile air into the stirred fermenter according to 10%-20% of the volume of the stirred fermenter;

wherein the fed-batch nutrient components contain a carbon source, a nitrogen source and a phosphorus source, wherein the carbon source is one or a combination of glucose, fructose syrup, and starch hydrolyzate, the nitrogen source is one or a combination of potassium nitrate, sodium nitrate, ammonium chloride, ammonium sulfate, urea, yeast extract, and peptone, and the phosphorus source is one or a combination of potassium phosphate and its hydrate, potassium hydrogen phosphate and its hydrate, potassium dihydrogen phosphate and its hydrate, sodium phosphate and its hydrate, sodium hydrogen phosphate and its hydrate, and sodium dihydrogen phosphate and its hydrate;

step C, transferring fucoxanthin fermentation broth prepared in the step B into a photobioreactor under the irradiation of monochromatic light or mixed light, and obtaining high fucoxanthin induction culture solution by aeration induction culture under autophototrophic culture conditions, wherein loading capacity of the fucoxanthin fermentation broth is 20%-80%, the culture temperature is 20-30 degree Celsius, the induction period is 1-4 days; the light intensity is not more than 200 $\mu mol \cdot m^{-2} \cdot s^{-1}$, and the light source is monochromatic light or blue-white mixed light with the ratio of blue light and white light of 0-1:0-1;

step D, extracting fucoxanthin from the high fucoxanthin induction culture solution obtained after the end of fermentation of the step C.

Preferably, in the step B, wherein the mass ratio of the carbon source, the nitrogen source, and the phosphorus source in the fed-batch nutrient components is 52-141:5.6-21.1:1.

Preferably, in the step B, the carbon source, the nitrogen source, and the phosphorus source in the fed-batch nutrient components are added by way of proportionally alone or in combination of at least two of the fed-batch nutrient components.

Preferably, in the step B, the culture mean of fed-batch nutrient components is that a feed liquid prepared through mixing of the carbon source, the nitrogen source and the phosphorus source of the fed-batch nutrient components in a proportion is fed into sterile fermentation medium of the reaction vessel, wherein the carbon source concentration is glucose as a standard, the glucose concentration is 100 g/L-500 g/L, the nitrogen source concentration is 22.7 g/L-113.4 g/L, and the phosphorus source concentration is 3.3 g/L-16.6 g/L.

Preferably, the sterile inocula culture medium and the sterile fermentation medium all include the following raw materials in a mass concentration:

NaCl: 10 g/L-32 g/L; $MgSO_4 \cdot 7H_2O$: 1.09 g/L-2.18 g/L;
$CaCl_2 \cdot 2H_2O$: 0.1 g/L-0.27 g/L; $FeCl_3 \cdot 6H_2O$: 0.291 mg/L-0.582 mg/L;
$MnCl_2 \cdot 4H_2O$: 0.025 mg/L-0.246 mg/L; $ZnCl_2$: 0.031 mg/L-0.311 mg/L;
$CoCl_2 \cdot 6H_2O$: 0.0114 mg/L-0.0228 mg/L;
$Na_2MoO_4 \cdot 2H_2O$: 0.012 mg/L-0.024 mg/L; $H_3BO_3$: 3.06 mg/L-30.56 mg/L;
$(NH_4)_6Mo_7O_{24} \cdot 4H_2O$: 0.028 mg/L-0.278 mg/L;
Tris-buffer: 0.089 g/L-0.892 g/L; $H_2SO_4$: 1.64 µg/L-16.4 µg/L;

Vitamin $B_{12}$: 1.5 g/L-15×$10^{-5}$ g/L; biotin: 2.5 g/L-25×$10^{-5}$ g/L;
$Na_2SiO_3$: 0.064 g/L-2.0 g/L; pH=6-9.5;
carbon source: 1 g/L-20 g/L; nitrogen source: 0.3 g/L-3 g/L; phosphate: 40 mg/L-1000 mg/L;

wherein the carbon source is one or a combination of two or more of glucose, fructose syrup, and starch hydrolyzate, the nitrogen source is one or a combination of two or more of potassium nitrate, sodium nitrate, ammonium chloride, ammonium sulfate, urea, yeast extract, and peptone, and the phosphorus source is one or a combination of two or more of potassium phosphate and its hydrate, potassium hydrogen phosphate and its hydrate, potassium dihydrogen phosphate and its hydrate, sodium phosphate and its hydrate, sodium hydrogen phosphate and its hydrate, and sodium dihydrogen phosphate and its hydrate.

Preferably, in the step B, wherein the reaction kettle of aeration fermentation is a stirred fermenter, stirring speed of stirred fermenter is 100-750 rpm during the aeration fermentation process, and sterile air is introduced into the stirred fermenter according to 10%-20% of the volume of the stirred fermenter.

Preferably, in the step B, wherein the reaction kettle of aeration fermentation is a stirred fermenter, stirring speed of stirred fermenter is 200-700 rpm during the aeration fermentation process, and the ventilation of sterile air is 1-3 liters/minute.

Preferably, the culture mean of fed-batch nutrient components includes continuous fed-batch and intermittent fed-batch.

Preferably, the culture mean of fed-batch nutrient components is intermittent fed-batch.

Preferably, in the step C, the condition of light induction culture is introducing sterile air with a volume of carbon dioxide below 5% into a column photobioreactor under the condition of light intensity of 5-200 $\mu mol \cdot m^{-2} \cdot s^{-1}$, wherein the ventilation of the sterile air is 3 liters/minute.

Preferably, in the step C, the condition of light induction culture is that the light intensity is 10 $\mu mol \cdot m^{-2} \cdot s^{-1}$, and the light source is white light or blue-white mixed light with the ratio of blue light and white light of 1:1.

Preferably, the nitrogen source in the sterile inocula culture medium and the sterile fermentation medium is selected from the following content range: the mass concentration of peptone being: 1 g/L; and the mass concentration range of the carbon source is as follows: the mass concentration of the carbon source being more than 5 g/L and not more than 50 g/L.

Preferably, the nitrogen source in the sterile inocula culture medium and the sterile fermentation medium is selected from the following content range: the mass concentration of peptone being 1 g/L; and the mass concentration range of the carbon source is as follows: the mass concentration of glucose being 5 g/L.

Preferably, in the step A, preparation of the inocula: placing activated algae *Nitzschia laevis* in a sterile inocula culture medium, performing heterotrophic culture for 3-8 days to prepare the inocula, making *Nitzschia laevis* cells in logarithmic growth phase.

The present invention at least comprises the following beneficial effects:

1. The present invention firstly proposes a method for preparing a high cell density *Nitzschia laevis* fermentation broth by using a fed-batch method. It has been confirmed by the applicant's experiment that heterotrophic culture high-density *Nitzschia laevis* by the established fermentation model can obtain high cell density (at least 5 g/L, up to 17.25 g/L), which is 2.83 times higher than the prior art (currently reported up to 4.5 g/L), and the productivity of fucoxanthin is very high (at least 5.5 mg/(L·d), up to 16.5 mg/(L·d), which is 3.98 times higher than the prior art. Afterwards, the present invention further proposes to use a light source of different light quality to induce the Nitzschia laevis fermentation broth to improve the fucoxanthin content. It has been confirmed by the applicant's experiment that the content of fucoxanthin in the prepared dried alga powder of Nitzschia laevis is very high (at least 0.8-1.0%, up to 1.19%, which is 20% higher than the prior art, up to 58.7%). In summary, the invention can greatly increase the productivity of fucoxanthin under the premise of obtaining high cell density and high content of fucoxanthin to meet the needs of industrial production of fucoxanthin.

2. The method provided by the present invention has the potential to be applied to the industrial production of fucoxanthin. Firstly, the fucoxanthin content and cell density of the Nitzschia laevis were greatly improved after optimizing the culture conditions. Secondly, the fucoxanthin productivity was much higher than all the diatoms and other algae reported so far.

3. The alga powder of Nitzschia laevis obtained by the present invention can stably realize continuous industrial production without being restricted by external conditions, and can control common marine pollutants such as heavy metals and polychlorinated biphenyls from the source of the culture medium. The source of fucoxanthin is safer than seaweeds.

4. Compared with production of fucoxanthin by other microalgae culture, the production cycle is greatly shortened, and the fermentation can be completed in the shortest time of 3 days. While increasing production efficiency, reducing production cost, and greatly reducing pollution risk during the culture process.

Other advantages, objects, and features of the present invention will be showed in part through following description, and in part will be understood by those skilled in the art from study and practice of the present invention.

Figure 2:
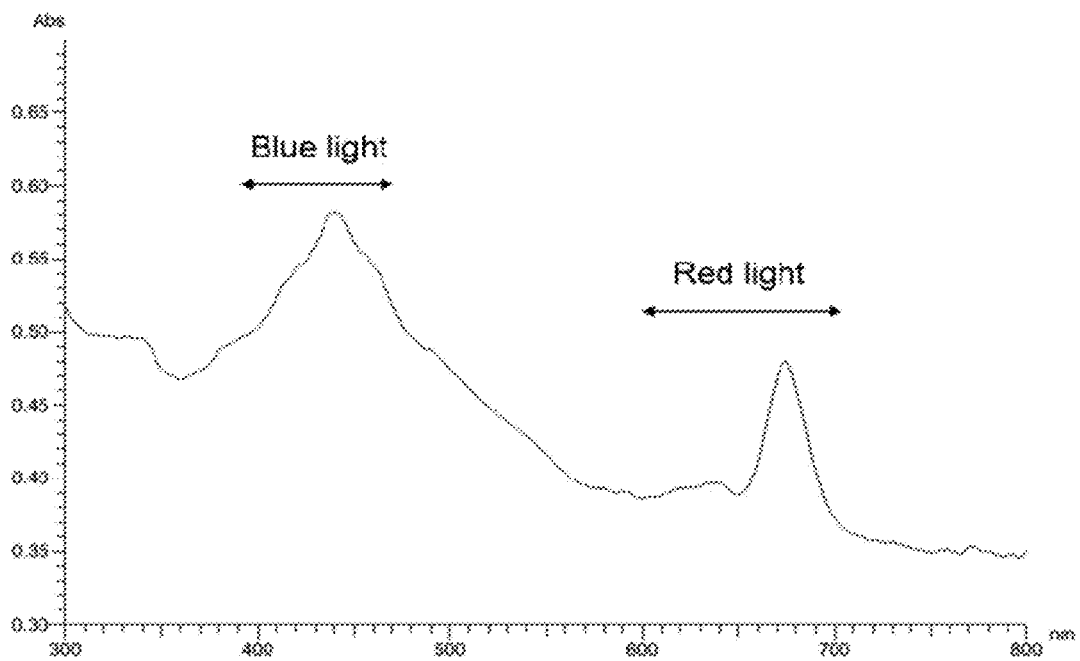
FIG. 2 is a spectrum of Nitzschia laevis cells after fermentation at 300-800 nm under UV-Vis spectrophotometer.

It can be seen from FIG. 2 that the Nitzschia laevis cells have two significant absorption peaks at 440 nm and 674 nm, which indicates that the cells have stronger absorption of blue light and red light. This result provides a basis for selecting a suitable wavelength to induce Nitzschia laevis.

Figure 3:
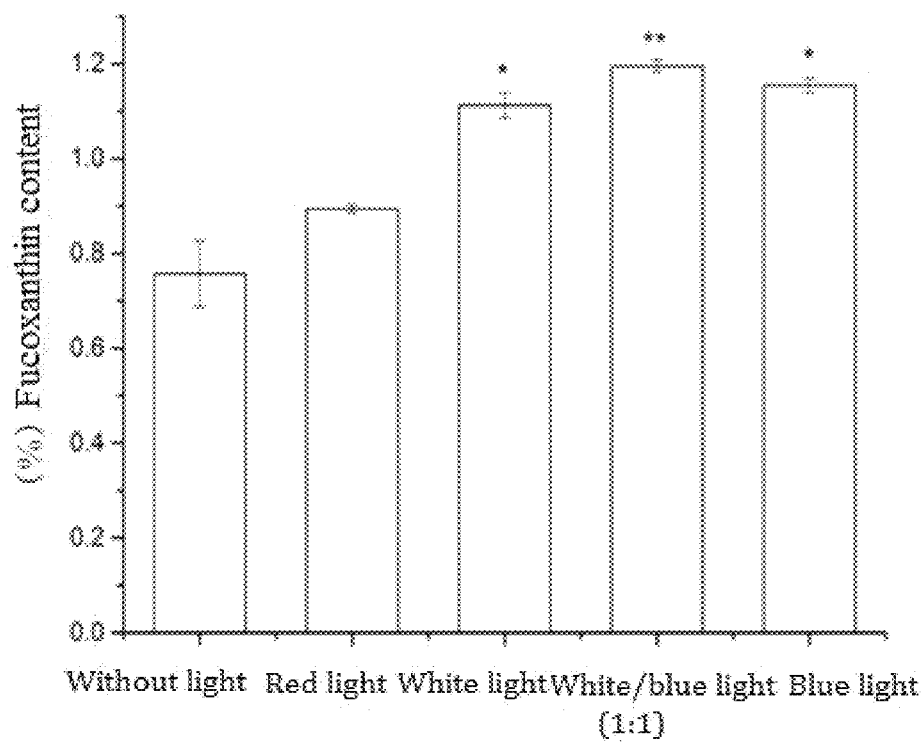

FIG. 3 is a comparison view of fucoxanthin content after induced Nitzschia laevis cells with different light qualities (light intensity of 10 μmol·m$^{-2}$·s$^{-1}$) after fermentation.

It can be seen from the figure that the fucoxanthin content of the Nitzschia laevis cells is only 0.75% (accounting for dry weight of cells) under dark conditions. Red light has no significant effect on the accumulation of fucoxanthin, and white light and blue light significantly increase the fucoxanthin content to 1.09% and 1.11%, respectively, while the mixed light of blue light and white light (1:1) is most significant for increasing the fucoxanthin content, which is up to 1.19%.

Figure 4:
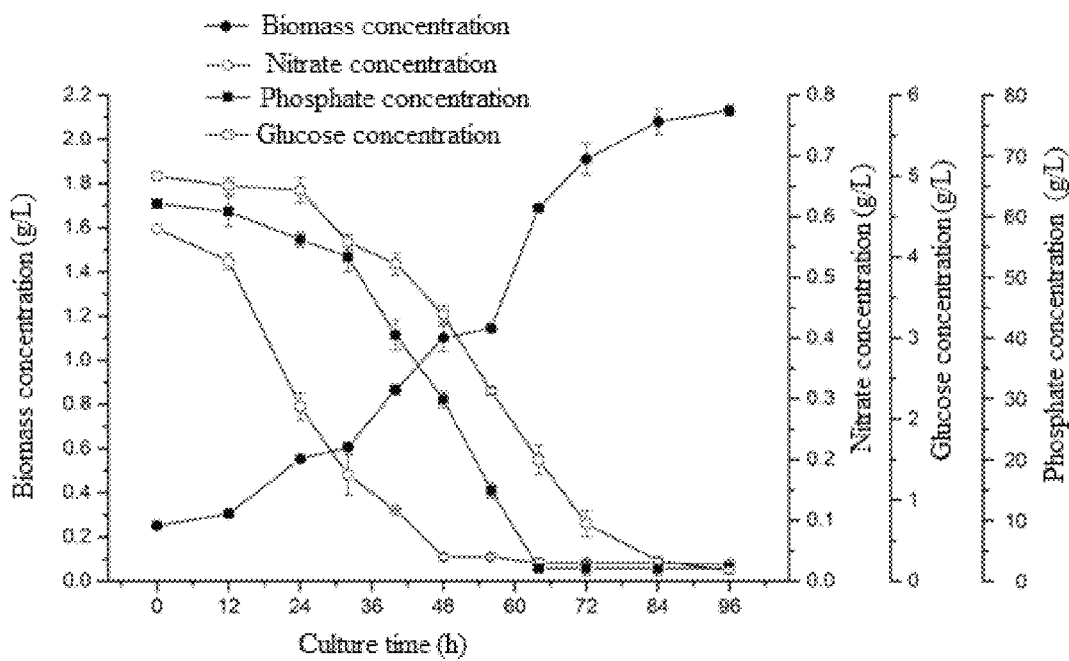

FIG. 4 is a graph showing the relationship between the consumption rate of carbon source, nitrogen source and phosphorus source and the concentration of cells in the process of fed-batch culture of Nitzschia laevis.

When culturing in a shake flask, the cells began to enter the plateau phase at 72 h, while the nitrogen source was consumed at 48 h, the phosphorus source was consumed at 64 h, and the glucose was consumed at 84 h. According to the rate of nutrient consumption and cell growth rate, 12 h-72 h was determined as the logarithmic growth phase of the cells. The substrate conversion rates of carbon source, nitrogen source and phosphorus sources were 0.35 g/g, 2.60 g/g and 32.21 g/g, respectively.

Figure 5:
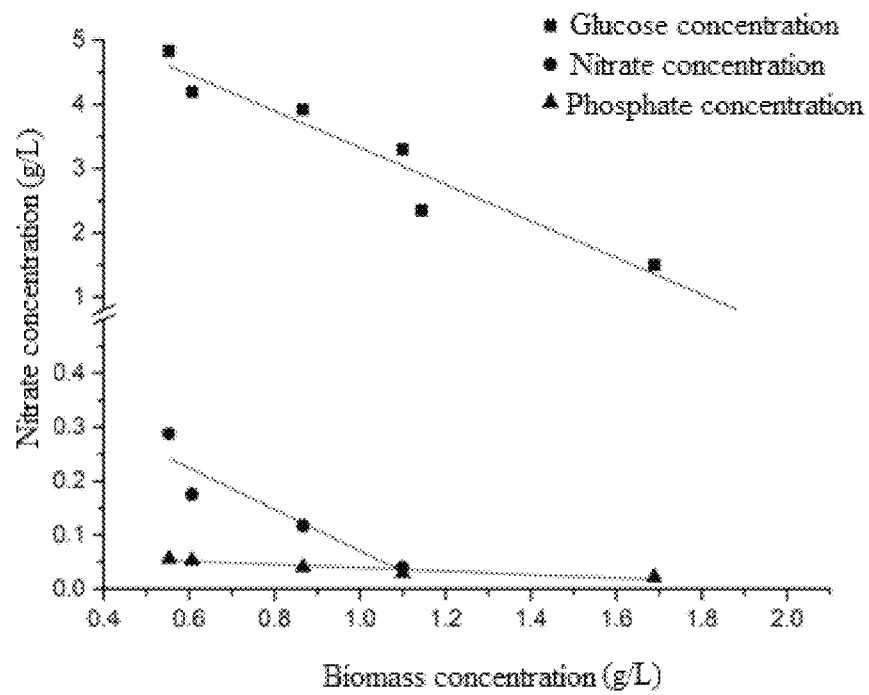

FIG. 5 is a graph showing the relationship between the growth concentration of Nitzschia laevis cells relative to the concentration in the fed-batch nutrient component.

According to the consumption rate of the three main substrates and cell growth rate, calculating the ratio of the carbon source, nitrogen source, and phosphorus source ratio was 91.55:12.37:1.00, and the feed liquid was prepared according to the ratio for feed-batch fermentation process.

Figure 6:
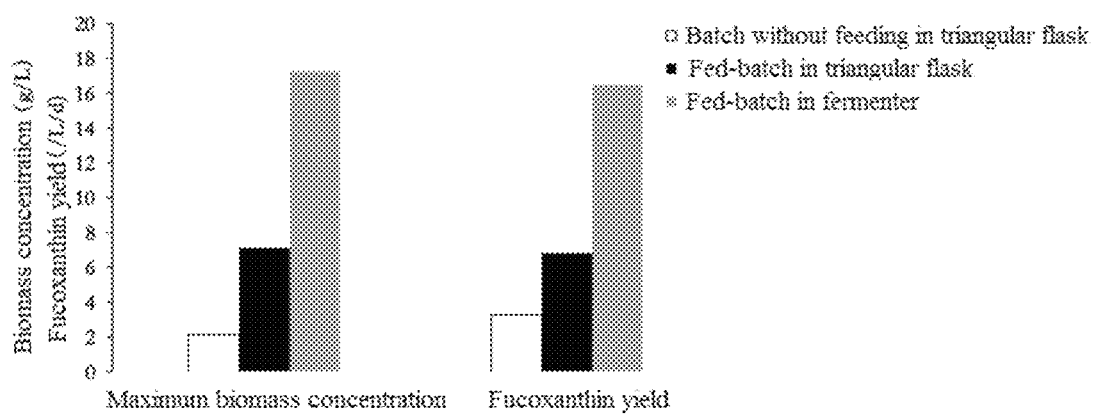

FIG. 6 is a graph showing the highest biomass concentration and fucoxanthin productivity in three conditions: batch fermentation culture without feeding of Nitzschia laevis in triangular flask, fed-batch fermentation culture in triangular flask, and fed-batch fermentation culture of in fermenter.

It can be seen from the figure that the cell density is only 2.13 g/L in batch fermentation culture without feeding of Nitzschia laevis in triangular flask, and the cell density is significantly increased under the conditions of fed-batch culture in triangular flask, up to 7.13 g/L. When fed-batch fermentation culture in fermenter, the biomass is up to 17.25 g/L, which is 3.83 times the highest cell density of the current reported technology. At this time, the concentration of fucoxanthin in the cells is as high as 0.96% (accounting for dry weight of cells). The fucoxanthin productivity was 16.5 mg/(L·d), which was 4.98 times the highest productivity of the prior art.

DETAILED DESCRIPTION

The present invention will now be described in further detail with reference to the accompanying drawings and embodiments in order to enable person skilled in the art to practice with reference to the description.

It should be noted that in the description of the present invention, the terms of "having", "comprising" and "including" do not match the existence or addition of one or more other elements or their combinations.

The detection methods involved in the present invention are as follows:

1. Determination of Dry Weight of Nitzschia Laevis Cells

Taking 3 mL of fermentation broth every 24 hours after inoculation, and centrifuging for 5 minutes at a speed of 3000 rpm, washing with ddH$_2$O and re-centrifuging twice, repeating 2 times, and filtering the fermentation broth onto a pre-weighed filter paper and placing in 80 degree Celsius vacuum oven for drying to constant weight.

2. Determination of Fucoxanthin

At present, the applicant has not found the national or enterprise standard for fucoxanthin detection, mainly by Ultraviolet visible light absorption (UV method) and high performance liquid chromatography (HPLC). Because of the poor specificity of UV method, it is susceptible to interference from other pigments. Therefore, the HPLC method is a better detection method for fucoxanthin. This application refers to the research of Guo et al. and improves on the basis of the research, including as follows:

Weighing 20 mg of freeze-dried alga powder, milling at low temperature, adding 5 mL of absolute ethanol, performing shake extraction for 10 minutes, centrifuging (condition: temperature of 4 degree Celsius, rotation speed of 3000 rpm, time of 5 minutes), collecting the supernatant, re-adding 3 mL of absolute ethanol in the precipitate, performing shake extraction until the algal powder was white, collecting extract, centrifuging at a temperature of 4 degree Celsius and a rotation speed of 12,000 rpm for 10 minutes, collecting supernatant, blow-drying with nitrogen gas, and then adding 1 mL of absolute ethanol to dissolve pigment, after passing through membrane, performing high performance liquid chromatography (HPLC) analysis, wherein the whole process is carried out in the dark.

3. HPLC Analysis Method

High performance liquid chromatography Waters 2695, which is equipped with a PDA detector with a detection wavelength of 450 nm, using a C18 reverse phase column (250 mm×4.6 mm×5 mm). The mobile phase was: phase A was pure ethyl acetate, phase B was acetonitrile, methanol and water with the ratio of 84:2:14, and phase C was pure methanol, using gradient elution, wherein all mobile phase was HPLC grade.

Embodiment 1

Figure 1:
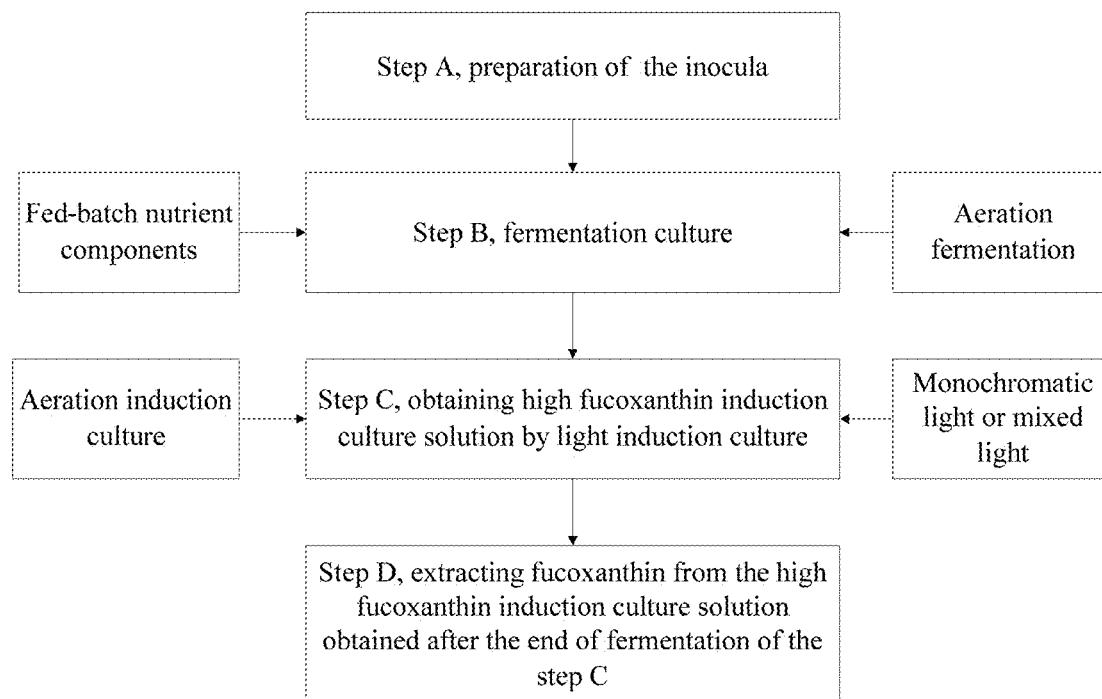
FIG. 1 is a flow diagram of the fermentation method for production of fucoxanthin by Nitzschia laevis according to the present invention.

As shown in FIG. 1 of the drawings, the present invention provides a fermentation method for production of fucoxanthin by *Nitzschia laevis*, including the following steps of:

step A, preparation of the inocula: placing activated alga *Nitzschia laevis* in a sterile inocula culture medium, performing heterotrophic culture for 2 days to prepare the inocula, making *Nitzschia laevis* cells in logarithmic growth phase, wherein the alga *Nitzschia laevis* is *Nitzschia laevis* UTEX 2047, wherein the *Nitzschia laevis* is selected from *Nitzschia laevis* UTEX 2047 (purchased from Culture Collection of Algae at The University of Texas at Austin, abbreviating UTEX).

step B, fermentation culture: inoculating of *Nitzschia laevis* in the logarithmic growth phase of the step A according to a volume ratio of 10% to a reaction kettle containing a sterile fermentation medium for aeration fermentation, preparing fucoxanthin fermentation broth through culture mean of fed-batch nutrient components, wherein the temperature is 20 to 30 degree Celsius in the aeration fermentation process, the fermentation cycle is 2-14 days, the dissolved oxygen of the fermentation medium is not less than 20%, pH is 6-9, and the concentration of glucose, nitrate and phosphate in the fermentation medium is 1-10 g/L, 0.1-1.5 g/L and 10-100 mg/L, respectively; or performing shake culture in a triangular flask with a stirring speed of 100-300 rpm, culture temperature of 20 to 30 degree Celsius, and culture cycle of 3-12 days;

wherein the fed-batch nutrient components contain a carbon source, a nitrogen source and a phosphorus source, wherein the carbon source is one or a combination of glucose, fructose syrup, and starch hydrolyzate, the nitrogen source is one or a combination of potassium nitrate, sodium nitrate, ammonium chloride, ammonium sulfate, urea, yeast extract, and peptone, and the phosphorus source is one or a combination of potassium phosphate and its hydrate, potassium hydrogen phosphate and its hydrate, potassium dihydrogen phosphate and its hydrate, sodium phosphate and its hydrate, sodium hydrogen phosphate and its hydrate, and sodium dihydrogen phosphate and its hydrate;

wherein the sterile inocula culture medium and the sterile fermentation medium all include the following raw materials in a mass concentration:

NaCl: 10 g/L-32 g/L; $MgSO_4 \cdot 7H_2O$: 1.09 g/L-2.18 g/L;

$CaCl_2 \cdot 2H_2O$: 0.1 g/L-0.27 g/L; $FeCl_3 \cdot 6H_2O$: 0.291 mg/L-0.582 mg/L;

$MnCl_2 \cdot 4H_2O$: 0.025 mg/L-0.246 mg/L; $ZnCl_2$: 0.031 mg/L-0.311 mg/L;

$CoCl_2 \cdot 6H_2O$: 0.0114 mg/L-0.0228 mg/L;

$Na_2MoO_4 \cdot 2H_2O$: 0.012 mg/L-0.024 mg/L; $H_3BO_3$: 3.06 mg/L-30.56 mg/L;

$(NH_4)_6MO_7O_{24} \cdot 4H_2O$: 0.028 mg/L-0.278 mg/L;

Tris-buffer: 0.089 g/L-0.892 g/L; $H_2SO_4$: 1.64 μg/L-16.4 μg/L;

Vitamin $B_{12}$: 1.5 g/L-15×10$^{-5}$ g/L; biotin: 2.5 g/L-25×10$^{-5}$ g/L;

$Na_2SiO_3$: 0.064 g/L-2.0 g/L; pH=6-9.5;

carbon source: 1 g/L-20 g/L; nitrogen source: 0.3 g/L-3 g/L; phosphate: 40 mg/L-1000 mg/L;

wherein the carbon source is one or a combination of two or more of glucose, fructose syrup, and starch hydrolyzate, the nitrogen source is one or a combination of two or more of potassium nitrate, sodium nitrate, ammonium chloride, ammonium sulfate, urea, yeast extract, and peptone, and the phosphorus source is one or a combination of two or more of potassium phosphate and its hydrate, potassium hydrogen phosphate and its hydrate, potassium dihydrogen phosphate and its hydrate, sodium phosphate and its hydrate, sodium hydrogen phosphate and its hydrate, and sodium dihydrogen phosphate and its hydrate;

step C, transferring fucoxanthin fermentation broth prepared in the step B into a photobioreactor under the irradiation of monochromatic light or mixed light, and obtaining high fucoxanthin induction culture solution by aeration induction culture under autophototrophic culture conditions, wherein loading capacity of the fucoxanthin fermentation broth is 60%, the culture temperature is 23 degree Celsius, the induction period is 2 days; the light intensity is not more than 200 μmol·m$^{-2}$·s$^{-1}$, and the light source is monochromatic light or blue-white mixed light with the ratio of blue light and white light of 0-1:0-1 (as shown in FIG. 2-FIG. 3);

step D, extracting fucoxanthin from the high fucoxanthin induction culture solution obtained after the end of fermentation of the step C, specifically, centrifuging the high fucoxanthin induction culture solution, and freeze-drying.

The rest of the content is as mentioned above.

Embodiment 2

The difference between this embodiment and the embodiment 1 is that the alga *Nitzschia laevis* in the present embodiment is selected from *Nitzschia laevis* CCMP559 (purchased from National Center for Marine Algae and Microbiota, abbreviating NCMA).

Embodiment 3

The difference between this embodiment and the embodiment 1 is that the alga *Nitzschia laevis* in the present embodiment is selected from *Nitzschia laevis* CCMP 1092 (purchased from National Center for Marine Algae and Microbiota, abbreviating NCMA).

Effect Analysis:

The content of fucoxanthin of *Nitzschia laevis* was up to 1.19% (accounting for dry weight of cells) under the culture condition of mixed light (blue light and white light with ratio of 1:1), which was 58.7% higher than that of matte heterotrophic fermentation.

Embodiment 4

The difference between this embodiment and the embodiment 3 is that the loading capacity of the fucoxanthin fermentation broth is 20%, the light intensity of the mixed light is 60 $\mu mol \cdot m^{-2} \cdot s^{-1}$, and the temperature of induction culture is 23 degree Celsius.

Effect Analysis:

The fucoxanthin accumulation of production strain in this embodiment is better, and the content of fucoxanthin was 1.1%.

Embodiment 5

The difference between this embodiment and the embodiment 1 is that the photobioreactor uses a 700 mL column photobioreactor, the loading capacity of the fucoxanthin fermentation broth is 560 mL (loading capacity of 80%), the light intensity is 20 $\mu mol \cdot m^{-2} \cdot s^{-1}$, the ventilation is 3 liters/minute, and the induction period is 4 days. The rest is the same as in the embodiment 1.

Embodiments 6-12

The difference between embodiments 6-12 and the embodiment 4 is that the ratio of the blue light and the white light in the mixed light of embodiments 6-12 is 0:1, 1:10, 1:6, 1:1, 4:1, 10:1, 1:0, respectively, and the induction period is 2 days.

Effect Analysis of Embodiments 5-12:

Referring to FIG. 4, the mixed light induction treatment can further increase the fucoxanthin content, further increasing fucoxanthin content, and the fucoxanthin content is up to 1.10%.

Embodiments 13 transferring *Nitzschia laevis* fermentation broth prepared in the step B of the embodiments 1 into a photobioreactor under the irradiation of mixed light, performing aeration induction culture under autophototrophic culture conditions. A 700 mL column photosynthetic reactor was used as a culture vessel, transferring *Nitzschia laevis* fermentation broth after heterotrophic culture into 500 mL (loading capacity of 71.4%). The induced condition was blue-white mixed light with the ratio of blue light and white light of 1:1, the light intensity is 10 $\mu mol \cdot m^{-2} \cdot s^{-1}$, the light source used for light is LED light or a combination thereof, the gas is sterile air with ventilation of 3 liters/min, the temperature of the induction culture is 23 degree Celsius, and the induction culture period is 1 day.

Embodiments 14-16

The difference between embodiments 14-16 and the embodiment 13 is that the light intensity in embodiments 14-16 is 5, 100, 200 $\mu mol \cdot m^{-2} \cdot s^{-1}$, respectively.

Effect Analysis:

fucoxanthin content of the *Nitzschia laevis* cells in the fermentation broth was significantly increased under the irradiation of mixed light with the ratio of blue light and white light of 1:1. Increased range was from 20% to 58.7%, and the highest content of fucoxanthin was 1.19%.

Embodiments 17-19

The difference between embodiments 17-19 and the embodiment 13 is that carbon dioxide accounts for 5%, 2.5% and 1% by volume of sterile air during sterile air introduction process of embodiments 17-19.

Effect Analysis:

fucoxanthin content of the *Nitzschia laevis* cells increased from 30% to 50% after introducing sterile air with different carbon dioxide concentrations.

Embodiments 20 transferring *Nitzschia laevis* fermentation broth prepared in the step A of the embodiments 1 into a photobioreactor under the irradiation of mixed light, performing aeration induction culture under autophototrophic culture conditions. A 700 mL column photosynthetic reactor was used as a culture vessel, transferring *Nitzschia laevis* fermentation broth after heterotrophic culture into 500 mL (loading capacity of 71.4%). The induced condition was white light, the light intensity is 20 $\mu mol \cdot m^{-2} \cdot s^{-1}$, the light source used for light is sunlight, the gas is sterile air with ventilation of 3 liters/min, the temperature of the induction culture is 23 degree Celsius, and the induction culture period is 1 day.

Embodiments 21-22

The difference between embodiments 21-22 and the embodiment 20 is that the light source of embodiments 21-22 is a fluorescent lamp, the light intensity is 5 $\mu mol \cdot m^{-2} \cdot s^{-1}$ and 20 $\mu mol \cdot m^{-2} \cdot s^{-1}$, respectively, and the temperature of the induction culture is 20 degree Celsius and 23 degree Celsius.

Effect Analysis:

fucoxanthin content of the *Nitzschia laevis* cells in the fermentation broth was significantly increased under different light sources and different light intensities. Increased range was from 30% to 58%, and the highest content of fucoxanthin was 1.18%.

The applicant also performs the following test and detection on the intermittent fed-batch nutrient component in the fermentation culture process of the step B in the above embodiment, and the test result is as shown in FIG. 4-6, specifically including the following embodiments:

Embodiment 23

In the embodiment, the alga *Nitzschia laevis* is *Nitzschia laevis* UTEX 2047, including the following steps of:

step A, preparation of the inocula:

placing activated alga *Nitzschia laevis* in a sterile inocula culture medium, performing heterotrophic culture for 2 days to prepare the inocula, making *Nitzschia laevis* cells in logarithmic growth phase;

step B, fermentation culture:

inoculating of *Nitzschia laevis* in the logarithmic growth phase of the step A according to a volume ratio of 10% to a triangular flask containing a sterile fermentation medium for shake culture to prepare fermentation broth, culturing for 5 days at a culture temperature of 23 degree Celsius and a rotation speed of 150 rpm. The concentration of fed-batch carbon, nitrogen and phosphorus sources was controlled in the range of 1-10 g/L, 0.1-1.5 g/L and 10-100 mg/L, respectively. The preferred solution is to prepare a feed liquid having a concentration of carbon source, nitrogen source and phosphorus source of 500.0 g/L, 113.4 g/L and 16.6 g/L, respectively. According to fed-batch volume of the following Table 1:

TABLE 1

| Fermentation time | Fed-batch time point | Total fed-batch volume (mL) |
| --- | --- | --- |
| 0-24 h | Any time point within 0-24 h | 0.138 |
| 24-48 h | Any time point within 24-48 h | 0.268 |
| 48-72 h | Any time point within 48-72 h | 0.519 |
| 72-96 h | Any time point within 78-96 h | 1.007 |
| 96-120 h | Any time point within 110-120 h | 1.953 | wherein the sterile inocula culture medium and the sterile fermentation medium all include the following components in a mass concentration:

NaCl: 10 g/L; $MgSO_4 \cdot 7H_2$: 2.18 g/L; $CaCl_2 \cdot 2H_2O$: 0.1 g/L; $FeCl_3 \cdot 6H_2O$: 0.582 mg/L; $MnCl_2 \cdot 4H_2O$: 0.123 mg/L; $ZnCl_2$: 0.311 mg/L; $CoCl_2 \cdot 6H_2O$: 0.0228 mg/L; $Na_2MoO_4 \cdot 2H_2O$: 0.018 mg/L; $H_3BO_3$: 30.56 mg/L; $(NH_4)_6 MO_7O_{24} \cdot 4H_2O$: 0.028 mg/L; Tris-buffer: 0.892 g/L; $H_2SO_4$: 8.2 µg/L; Vitamin $B_{12}$: $15 \times 10^{-5}$ g/L; biotin: $25 \times 10^{-5}$ g/L; $Na_2SiO_3$: 0.96 g/L; $NaNO_3$ 0.3 g/L; $KH_2PO_4$ 40 mg/L: glucose 1 g/L, pH=6;

extracting of fucoxanthin from the fermentation broth after the end of the fermentation in step B and detecting by HPLC.

Effect Analysis:

*Nitzschia laevis* UTEX 2047 grew better under heterotrophic culture fed-batch conditions, which has a biomass of up to 7.13 g/L and a fucoxanthin productivity of 6.82 mg/(L·d) under heterotrophic conditions. The highest fucoxanthin productivity of the currently reported heterotrophic culture of *Nitzschia laevis* is 3.31 mg/(L·d). The embodiment is an increase of 106.7% compared with the prior art.

Embodiment 24

Heterotrophic Culture of the *Nitzschia laevis* in a Triangular Flask

In the embodiment, the alga *Nitzschia laevis* is *Nitzschia laevis* CCMP559, including the following steps of:

step A, preparation of the inocula:

placing activated alga *Nitzschia laevis* in a sterile inocula culture medium, performing heterotrophic culture for 7 days to prepare the inocula, making *Nitzschia laevis* cells in logarithmic growth phase;

step B, fermentation culture:

inoculating of *Nitzschia laevis* in the logarithmic growth phase of the step A according to a volume ratio of 20% to a 1 L triangular flask containing 400 mL sterile fermentation medium for shake culture to prepare fermentation broth, culturing for 5 days at a culture temperature of 30 degree Celsius and a rotation speed of 240 rpm. The concentration of fed-batch carbon, nitrogen and phosphorus sources was controlled in the range of 1-10 g/L, 0.1-1.5 g/L and 10-100 mg/L, respectively. The preferred solution is to prepare a feed liquid having a concentration of carbon source, nitrogen source and phosphorus source of 300.0 g/L, 68.0 g/L and 9.96 g/L, respectively. According to fed-batch volume of the following Table 2:

TABLE 2

| Fermentation time | Fed-batch time point | Total fed-batch volume (mL) |
| --- | --- | --- |
| 0-24 h | Any time point within 0-24 h | 0.23 |
| 24-48 h | Any time point within 24-48 h | 0.45 |
| 48-72 h | Any time point within 48-72 h | 0.87 |
| 72-96 h | Any time point within 78-96 h | 1.68 | wherein the sterile inocula culture medium and the sterile fermentation medium all include the following components:

NaCl: 32 g/L; $MgSO_4 \cdot 7H_2O$: 1.09 g/L; $CaCl_2 \cdot 2H_2O$: 0.15 g/L; $FeCl_3 \cdot 6H_2O$: 0.402 mg/L; $MnCl_2 \cdot 4H_2O$: 0.025 mg/L; $ZnCl_2$: 0.132 mg/L; $CoCl_2 \cdot 6H_2O$: 0.0332 mg/L; $Na_2MoO_4 \cdot 2H_2$: 0.024 mg/L; $H_3BO_3$: 3.06 mg/L; $(NH_4)_6 MO_7O_{24} \cdot 4H_2O$: 0.278 mg/L; Tris-buffer: 0.089 g/L; $H_2SO_4$: 8.2 µg/L; Vitamin $B_{12}$: $7.5 \times 10^{-5}$ g/L; biotin: $12.5 \times 10^{-5}$ g/L; $Na_2SiO_3$: 0.064 g/L; $NaNO_3$ 1 g/L; $KH_2PO_4$ 400 mg/L; glucose 10 g/L, pH=8.2;

extracting of fucoxanthin from the fermentation broth after the end of the fermentation in step B and detecting by HPLC.

Effect Analysis:

*Nitzschia laevis* CCMP559 grew better under heterotrophic culture fed-batch conditions, which has a biomass of up to 6.92 g/L. The embodiment is an increase of 97.0% compared with the prior art.

Embodiment 25

Heterotrophic Culture of the *Nitzschia laevis* in a Triangular Flask.

In the embodiment, the alga *Nitzschia laevis* is *Nitzschia laevis* CCMP1092, including the following steps of:

step A, preparation of the inocula:

placing activated alga *Nitzschia laevis* in a sterile inocula culture medium, performing heterotrophic culture for 5 days to prepare the inocula, making *Nitzschia laevis* cells in logarithmic growth phase;

step B, fermentation culture:

inoculating of *Nitzschia laevis* in the logarithmic growth phase of the step A according to a volume ratio of 3% to a 5 L triangular flask containing 2 L sterile fermentation medium for shake culture to prepare fermentation broth, culturing for 5 days at a culture temperature of 20 degree Celsius and a rotation speed of 150 rpm. The concentration of fed-batch carbon, nitrogen and phosphorus sources was controlled in the range of 1-10 g/L, 0.1-1.5 g/L and 10-100 mg/L, respectively. The preferred solution is to prepare a feed liquid having a concentration of carbon source, nitrogen source and phosphorus source of 100.0 g/L, 22.68 g/L and 3.32 g/L, respectively. According to fed-batch volume of the following Table 3:

TABLE 3

| Fermentation time | Fed-batch time point | Total fed-batch volume (mL) |
| --- | --- | --- |
| 0-24 h | Any time point within 0-24 h | 0.69 |
| 24-48 h | Any time point within 24-48 h | 1.34 |
| 48-72 h | Any time point within 48-72 h | 2.595 |
| 72-96 h | Any time point within 78-96 h | 5.035 |
| 96-120 h | Any time point within 110-120 h | 9.765 | wherein the fermentation medium includes the following components:

NaCl: 16 g/L; $MgSO_4 \cdot 7H_2O$: 1.40 g/L; $CaCl_2 \cdot 2H_2O$: 0.27 g/L; $FeCl_3 \cdot 6H_2O$: 0.291 mg/L; $MnCl_2 \cdot 4H_2O$: 0.246 mg/L; $ZnCl_2$: 0.031 mg/L; $CoCl_2 \cdot 6H_2O$: 0.0114 mg/L; $Na_2MoO_4 \cdot 2H_2O$: 0.012 mg/L; $H_3BO_3$: 8.02 mg/L; $(NH_4)_6Mo_7O_{24} \cdot 4H_2O$: 0.154 mg/L; Tris-buffer: 0.446 g/L; $H_2SO_4$: 16.4 g/L; Vitamin $B_{12}$: $1.5 \times 10^{-5}$ g/L; biotin: $2.5 \times 10^{-5}$ g/L; $Na_2SiO_3$: 2 g/L; $NaNO_3$ 3 g/L; $KH_2PO_4$ 1000 mg/L; glucose 5 g/L, pH=9.5;

extracting of fucoxanthin from the fermentation broth after the end of the fermentation in step B and detecting by HPLC.

Effect Analysis:

*Nitzschia laevis* CCMP 1092 grew better under heterotrophic culture fed-batch conditions, which has a biomass of up to 6.2 g/L and a fucoxanthin productivity of 5.85 mg/(L·d) under heterotrophic conditions.

The highest fucoxanthin productivity of the currently reported heterotrophic culture of *Nitzschia laevis* is 3.31 mg/(L·d). The embodiment is an increase of 77.3% compared with the prior art.

Embodiment 26

Heterotrophic Culture of the *Nitzschia laevis* in a Fermenter.

In the embodiment, the alga *Nitzschia laevis* is *Nitzschia laevis* UTEX 2047, including the following steps of:

step A, preparation of the inocula:

placing activated alga *Nitzschia laevis* in a sterile inocula culture medium, performing heterotrophic culture for 5 days to prepare the inocula, making *Nitzschia laevis* cells in logarithmic growth phase;

step B, fermentation culture:

inoculating of *Nitzschia laevis* in the logarithmic growth phase of the step A according to a volume ratio of 10% to a fermenter containing a sterile fermentation medium for shake culture to prepare fermentation broth, culturing for 14 days at the conditions of a culture temperature of 23 degree Celsius, initial sterile air input of the fermenter being 10% of the fermenter volume per minute, the initial speed of the fermenter stirrer being 200 rpm, and the dissolved oxygen in the culture solution being not less than 30% (increasing the stirrer speed or ventilation when the dissolved oxygen is below 30%), pH being automatically adjusted to be constant at 8.2. The concentration of fed-batch carbon, nitrogen and phosphorus sources was controlled in the range of 1-10 g/L, 0.1-1.5 g/L and 10-100 mg/L, respectively. The preferred solution is to prepare a feed liquid having a concentration of carbon source, nitrogen source and phosphorus source of 500.0 g/L, 113.4 g/L and 16.6 g/L, respectively. According to fed-batch volume of the following Table 4:

TABLE 4

| Fermentation time | Fed-batch time point | Total fed-batch volume (mL) |
| --- | --- | --- |
| 0-24 h | Any time point within 0-24 h | 1.73 × fermentation broth volume (L) |
| 24-48 h | Any time point within 24-48 h | 3.4 × fermentation broth volume (L) |
| 48-72 h | Any time point within 48-72 h | 6.5 × fermentation broth volume (L) |

TABLE 4-continued

| Fermentation time | Fed-batch time point | Total fed-batch volume (mL) |
| --- | --- | --- |
| 72-96 h | Any time point within 78-96 h | 12.6 × fermentation broth volume (L) |
| 96-120 h | Any time point within 110-120 h | 24.4 × fermentation broth volume (L) |
| 120-144 h | Any time point within 120-144 h | 47.35 × fermentation broth volume (L) |
| 144-336 h | — | 0 | wherein the fermentation medium includes the following components:

NaCl: 10 g/L; $MgSO_4 \cdot 7H_2O$: 2.18 g/L; $CaCl_2 \cdot 2H_2O$: 0.1 g/L; $FeCl_3 \cdot 6H_2O$: 0.582 mg/L; $MnCl_2 \cdot 4H_2O$: 0.132 mg/L; $ZnCl_2$: 0.311 mg/L; $CoCl_2 \cdot 6H_2O$: 0.0228 mg/L; $Na_2MoO_4 \cdot 2H_2O$: 0.018 mg/L; $H_3BO_3$: 30.56 mg/L; $(NH_4)_6Mo_7O_{24} \cdot 4H_2O$: 0.028 mg/L; Tris-buffer: 0.892 g/L; $H_2SO_4$: 8.2 µg/L; Vitamin $B_{12}$: $15 \times 10^{-5}$ g/L; biotin: $25 \times 10^{-5}$ g/L; $Na_2SiO_3$: 0.96 g/L; $NaNO_3$ 0.3 g/L; $KH_2PO_4$ 40 mg/L; glucose 1 g/L, pH=6;

extracting of fucoxanthin from the fermentation broth after the end of the fermentation in step B and detecting by HPLC.

Effect Analysis:

*Nitzschia laevis* UTEX 2047 grew better under heterotrophic culture fed-batch conditions, which has a biomass of up to 17.25 g/L and a fucoxanthin productivity of 16.5 mg/(L·d) under heterotrophic conditions. The highest fucoxanthin productivity of the currently reported heterotrophic culture of *Nitzschia laevis* is 3.31 mg/(L·d). The embodiment is improved by 4.98 times compared with the prior art.

Embodiment 27

Heterotrophic Culture of the *Nitzschia laevis* in a Fermenter.

The difference between this embodiment and the embodiment 26 is that the initial sterile air input of the fermenter is 20% of the fermenter volume per minute, the initial speed of the fermenter stirrer is 400 rpm, the dissolved oxygen in the culture solution is not less than 30% (increasing the stirrer speed or ventilation when the dissolved oxygen is below 30%), and pH is automatically adjusted to be constant at 8.2, culturing for 14 days in the above conditions. The concentration of fed-batch carbon, nitrogen and phosphorus sources was controlled in the range of 1-10 g/L, 0.1-1.5 g/L and 10-100 mg/L, respectively. The preferred solution is to prepare a feed liquid having a concentration of carbon source, nitrogen source and phosphorus source of 300.0 g/L, 68.0 g/L and 9.96 g/L, respectively. According to fed-batch volume of the following Table 5:

TABLE 5

| Fermentation time | Fed-batch time point | Total fed-batch volume (mL) |
| --- | --- | --- |
| 0-24 h | Any time point within 0-24 h | 2.9 × fermentation broth volume (L) |
| 24-48 h | Any time point within 24-48 h | 5.7 × fermentation broth volume (L) |

TABLE 5-continued

| Fermentation time | Fed-batch time point | Total fed-batch volume (mL) |
|---|---|---|
| 48-72 h | Any time point within 48-72 h | 10.8 × fermentation broth volume (L) |
| 72-96 h | Any time point within 78-96 h | 21.0 × fermentation broth volume (L) |
| 96-120 h | Any time point within 110-120 h | 40.1 × fermentation broth volume (L) |
| 120-144 h | Any time point within 120-144 h | 78.9 × fermentation broth volume (L) |
| 144-336 h | — | 0 | wherein the fermentation medium includes the following components:

NaCl: 10 g/L; $MgSO_4 \cdot 7H_2O$: 2.18 g/L; $CaCl_2 \cdot 2H_2O$: 0.1 g/L; $FeCl_3 \cdot 6H_2O$: 0.582 mg/L; $MnCl_2 \cdot 4H_2O$: 0.132 mg/L; $ZnCl_2$: 0.311 mg/L; $CoCl_2 \cdot 6H_2O$: 0.0228 mg/L; $Na_2MoO_4 \cdot 2H_2O$: 0.018 mg/L; $H_3BO_3$: 30.56 mg/L; $(NH_4)_6 Mo_7O_{24} \cdot 4H_2O$: 0.028 mg/L; Tris-buffer: 0.892 g/L; $H_2SO_4$: 8.2 µg/L; Vitamin $B_{12}$: $15 \times 10^{-5}$ g/L; biotin: $25 \times 10^{-5}$ g/L; $Na_2SiO_3$: 0.96 g/L; $NaNO_3$ 0.3 g/L; $KH_2PO_4$ 40 mg/L; glucose 1 g/L, pH=6;

extracting of fucoxanthin from the fermentation broth after the end of the fermentation in step B and detecting by HPLC.

Effect Analysis:

*Nitzschia laevis* UTEX 2047 grew better under heterotrophic fed-batch conditions, which has a biomass of up to 16.1 g/L and a fucoxanthin productivity of 14.5 mg/(L·d) under heterotrophic conditions. The embodiment is improved by 3.38 times compared with the prior art.

Embodiment 28-30

Heterotrophic Culture of the *Nitzschia laevis* in a Fermenter.

The difference between embodiments 28-30 and the embodiment 27 is that the initial sterile air input of the fermenter in embodiments 28-30 is 12.5%, 15% and 17.5% of the fermenter volume per minute, respectively.

Effect Analysis:

*Nitzschia laevis* UTEX 2047 grew better under different sterile air input, which has a biomass of up to 15.4 g/L, 16.3 g/L and 16.5 g/L, respectively, and a fucoxanthin productivity of 13.2 mg/(L·d), 14.5 mg/(L·d) and 16.2 mg/(L·d) under heterotrophic conditions, respectively.

Embodiment 31

Heterotrophic Culture of the *Nitzschia laevis* in a Fermenter.

The difference between embodiments 31 and the embodiment 27 is that the fermentation medium includes the following components:

NaCl: 16 g/L; $MgSO_4 \cdot 7H_2O$: 1.40 g/L; $CaCl_2 \cdot 2H_2O$: 0.27 g/L; $FeCl_3 \cdot 6H_2O$: 0.291 mg/L; $MnCl_2 \cdot 4H_2O$: 0.246 mg/L; $ZnCl_2$: 0.031 mg/L; $CoCl_2 \cdot 6H_2O$: 0.0114 mg/L; $Na_2MoO_4 \cdot 2H_2O$: 0.012 mg/L; $H_3BO_3$: 8.02 mg/L; $(NH_4)_6 Mo_7O_{24} \cdot 4H_2O$: 0.154 mg/L; Tris-buffer: 0.446 g/L; $H_2SO_4$: 16.4 µg/L; Vitamin $B_{12}$: $1.5 \times 10^{-5}$ g/L; biotin: $2.5 \times 10^{-5}$ g/L; $Na_2SiO_3$: 2 g/L; $NaNO_3$ 3 g/L; $KH_2PO_4$ 1000 mg/L; glucose 5 g/L, pH=9.5;

Effect Analysis:

*Nitzschia laevis* UTEX 2047 grew better under medium components, which has a biomass of up to 15.9 g/L and a fucoxanthin productivity of 15.3 mg/(L·d) under heterotrophic conditions.

Embodiment 32

The difference between the embodiment 32 and the embodiment 27 is that the nitrogen source of the fermentation medium components is potassium nitrate, the phosphorus source is potassium dihydrogen phosphate, and the carbon source is fructose syrup.

Effect Analysis:

*Nitzschia laevis* UTEX 2047 grew better under medium components, which has a biomass of up to 14.8 g/L and a fucoxanthin productivity of 14.2 mg/(L·d) under heterotrophic conditions.

Embodiment 33-35

The difference between embodiments 33-35 and the embodiment 27 is that the nitrogen source of the fermentation medium components is a combination of urea and peptone, the phosphorus source is sodium hydrogen phosphate, and the carbon source is corn starch hydrolysate.

Effect Analysis:

*Nitzschia laevis* UTEX 2047 grew better under medium components, which has a biomass of up to 16.2 g/L and a fucoxanthin productivity of 16.8 mg/(L·d) under heterotrophic conditions.

In summary, the present invention firstly proposes a method for preparing a high cell density *Nitzschia laevis* fermentation broth by using a fed-batch method. It has been confirmed by the applicant's experiment that heterotrophic culture high-density *Nitzschia laevis* by the established fermentation model can obtain high cell density (at least 5 g/L, up to 17.25 g/L), which is 2.83 times higher than the prior art (currently reported up to 4.5 g/L), and the productivity of fucoxanthin is high (at least 5.5 mg/(L·d), up to 16.5 mg/(L·d), which is 3.98 times higher than the prior art. Afterwards, the present invention further proposes to use a light source of different light quality to induce the *Nitzschia laevis* fermentation broth to improve the fucoxanthin content. It has been confirmed by the applicant's experiment that the content of fucoxanthin in the prepared dried alga powder of *Nitzschia laevis* is high (at least 0.8-1.0%, up to 1.19%, which is 20% higher than the prior art, up to 58.7%). In summary, the invention can greatly increase the productivity of fucoxanthin under the premise of obtaining high cell density and high content of fucoxanthin to meet the needs of industrial production of fucoxanthin.

Although the embodiments of the present invention have been disclosed above, they are not limited to the applications previously mentioned in the specification and embodiments, and can be applied in various fields suitable for the present invention. For ordinary skilled person in the field, other various changed model, formula and parameter may be easily achieved without creative work according to instruction of the present invention, changed, modified and replaced embodiments without departing the general concept defined by the claims and their equivalent are still included in the present invention. The present invention is not limited to particular details and illustrations shown and described herein.

What is claimed is:

1. A fermentation method for production of fucoxanthin by *Nitzschia laevis*, comprising: the following steps of:

step A, preparation of an inocula:
placing activated alga *Nitzschia laevis* in a sterile inocula culture medium, performing heterotrophic culture for 2-11 days to prepare the inocula, making *Nitzschia laevis* cells in logarithmic growth phase, wherein the alga *Nitzschia laevis* is selected from *Nitzschia laevis* CCMP559, *Nitzschia laevis* UTEX 2047, or *Nitzschia laevis* CCMP 1092;

step B, fermentation culture:
inoculating of *Nitzschia laevis* in the logarithmic growth phase of the step A according to a volume ratio of 3%-20% to a reaction kettle containing sterile fermentation medium for an aeration fermentation process, performing fed-batch of nutrient components to the reaction kettle to prepare a fucoxanthin fermentation broth, wherein temperature is 20 to 30 degree Celsius in the aeration fermentation process, fermentation cycle is 2-14 days, dissolved oxygen of the sterile fermentation medium is not less than 20%, pH is 6-9, and the concentration of glucose, nitrate and phosphate in the sterile fermentation medium is 1-10 g/L, 0.1-1.5 g/L and 10-100 mg/L, respectively;

wherein fed-batch nutrient components contain a carbon source, a nitrogen source and a phosphorus source, wherein the carbon source is one or a combination of glucose, fructose syrup, and starch hydrolyzate, the nitrogen source is one or a combination of potassium nitrate, sodium nitrate, ammonium chloride, ammonium sulfate, urea, yeast extract, and peptone, and the phosphorus source is one or a combination of potassium phosphate and its hydrate, potassium hydrogen phosphate and its hydrate, potassium dihydrogen phosphate and its hydrate, sodium phosphate and its hydrate, sodium hydrogen phosphate and its hydrate, and sodium dihydrogen phosphate and its hydrate;

step C, transferring fucoxanthin fermentation broth prepared in the step B into a photobioreactor under irradiation of a light source of monochromatic light or mixed light, and obtaining high fucoxanthin induction culture solution by aeration induction culture under autophototrophic culture conditions, wherein loading capacity of the fucoxanthin fermentation broth is 20%-80%, culture temperature is 20-30 degree Celsius, induction period is 1-4 days; light intensity is not more than 200 $\mu mol \cdot m^{-2} \cdot s^{-1}$, and the light source is monochromatic light or blue-white mixed light with the ratio of blue light and white light of 0-1:0-1; and step D, extracting fucoxanthin from the high fucoxanthin induction culture solution obtained after the end of fermentation of the step C.

2. The fermentation method for production of fucoxanthin by *Nitzschia laevis* according to claim 1, wherein, the mass ratio of the carbon source, the nitrogen source, and the phosphorus source in the fed-batch nutrient components is 52-141: 5.6-21.1: 1 respectively in the step B.

3. The fermentation method for production of fucoxanthin by *Nitzschia laevis* according to claim 2, wherein, in the step B, the carbon source, the nitrogen source, and the phosphorus source in the fed-batch nutrient components are added proportionally; and the carbon source, the nitrogen source, and the phosphorus source are added individually, or at least two of the fed-batch nutrient components are combined and added.

4. The fermentation method for production of fucoxanthin by *Nitzschia laevis* according to claim 2, wherein, in the step B, the fed-batch of nutrient components is that a feed liquid prepared through mixing of the carbon source, the nitrogen source and the phosphorus source of the fed-batch nutrient components in a proportion is fed into a sterile fermentation medium of the reaction kettle, wherein the carbon source concentration is defined according to the glucose concentration, the glucose concentration is 100 g/L-500 g/L, the nitrogen source concentration is 22.7 g/L-113.4 g/L, and the phosphorus source concentration is 3.3 g/L-16.6 g/L.

5. The fermentation method for production of fucoxanthin by *Nitzschia laevis* according to claim 1, wherein, the sterile inocula culture medium and the sterile fermentation medium all include the following raw materials in a mass concentration:

NaCl: 10 g/L-32 g/L; $MgSO_4 \cdot 7H_2O$: 1.09 g/L-2.18 g/L; $CaCl_2 \cdot 2H_2O$: 0.1 g/L-0.27 g/L; $FeCl_3 \cdot 6H_2O$: 0.291 mg/L-0.582 mg/L;

$MnCl_2 \cdot 4H_2O$: 0.025 mg/L-0.246 mg/L; $ZnCl_2$: 0.031 mg/L-0.311 mg/L;

$CoCl_2 \cdot 6H_2O$: 0.0114 mg/L-0.0228 mg/L;

$Na_2MoO_4 \cdot 2H_2O$: 0.012 mg/L-0.024 mg/L; $H_3BO_3$: 3.06 mg/L-30.56 mg/L;

$(NH_4)_6MO_7O_{24} \cdot 4H_2O$: 0.028 mg/L-0.278 mg/L;

Tris-buffer: 0.089 g/L-0.892 g/L; $H_2SO_4$: 1.64 µg/L-16.4 µg/L;

Vitamin $B_{12}$: 1.5 g/L-15×$10^{-5}$ g/L; biotin: 2.5 g/L-25×$10^{-5}$ g/L;

$Na_2SiO_3$: 0.064 g/L-2.0 g/L; pH=6-9.5;

carbon source: 1 g/L-20 g/L; nitrogen source: 0.3 g/L-3 g/L;

wherein the carbon source is one or a combination of two or more of glucose, fructose syrup, and starch hydrolyzate, the nitrogen source is one or a combination of two or more of potassium nitrate, sodium nitrate, ammonium chloride, ammonium sulfate, urea, yeast extract, and peptone, and the phosphorus source is one or a combination of two or more of potassium phosphate and its hydrate, potassium hydrogen phosphate and its hydrate, potassium dihydrogen phosphate and its hydrate, sodium phosphate and its hydrate, sodium hydrogen phosphate and its hydrate, and sodium dihydrogen phosphate and its hydrate.

6. The fermentation method for production of fucoxanthin by *Nitzschia laevis* according to claim 1, wherein, the reaction kettle of aeration fermentation is a stirred fermenter, stirring speed of the stirred fermenter is 100-750 rpm during the aeration fermentation process, and sterile air is introduced into the stirred fermenter according to 10%-20% of a volume of the stirred fermenter in the step B.

7. The fermentation method for production of fucoxanthin by *Nitzschia laevis* according to claim 1, wherein, the reaction kettle of aeration fermentation is a stirred fermenter, stirring speed of the stirred fermenter is 200-700 rpm during the aeration fermentation process, and a ventilation of sterile air is 1-3 liters/minute in the step B.

8. The fermentation method for production of fucoxanthin by *Nitzschia laevis* according to claim 1, wherein, the fed-batch of nutrient components is selected from continuous fed-batch and intermittent fed-batch.

9. The fermentation method for production of fucoxanthin by *Nitzschia laevis* according to claim 1, wherein, the culture mean of fed-batch of nutrient components is intermittent fed-batch.

10. The fermentation method for production of fucoxanthin by *Nitzschia laevis* according to claim 1, wherein, in the step C, a condition of light induction culture is introducing sterile air with a volume of carbon dioxide below 5% into a column photobioreactor under a condition of light intensity of 5-200 $\mu mol \cdot m^{-2} \cdot s^{-1}$, wherein the ventilation of sterile air is 3 liters/minute.

11. The fermentation method for production of fucoxanthin by *Nitzschia laevis* according to claim 10, wherein, in the step C, the condition of light induction culture is that the light intensity is 10 $\mu mol \cdot m^{-2} \cdot s^{-1}$, and the light source is white light or blue-white mixed light with the ratio of blue light and white light of 1:1.

12. The fermentation method for production of fucoxanthin by *Nitzschia laevis* according to claim 1, wherein, the nitrogen source in the sterile inocula culture medium and the sterile fermentation medium is selected from the following content range: peptone: 1 g/L; and the mass concentration of the carbon source is more than 5 g/L and not more than 50 g/L.

13. The fermentation method for production of fucoxanthin by *Nitzschia laevis* according to claim 1, wherein, the nitrogen source in the sterile inocula culture medium and the sterile fermentation medium is selected from the following content range: peptone: 1 g/L; and the carbon source is selected from the following content range: glucose: 5 g/L.

14. The fermentation method for production of fucoxanthin by *Nitzschia laevis* according to claim 1, wherein, the heterotrophic culture is performed for 3-8 days in step A.

* * * * *